United States Patent [19]
Bar-Shavit

[11] Patent Number: 6,146,824
[45] Date of Patent: Nov. 14, 2000

[54] METHOD FOR DETERMINING TUMOR CELL ADHESION

[75] Inventor: Rachel Bar-Shavit, Jerusalem, Israel

[73] Assignee: Hadasit Medical Research Services and Development Company Ltd., Jerusalem, Israel

[21] Appl. No.: 08/981,088

[22] PCT Filed: Jun. 12, 1996

[86] PCT No.: PCT/IL96/00012

§ 371 Date: Jan. 27, 1998

§ 102(e) Date: Jan. 27, 1998

[87] PCT Pub. No.: WO97/00077

PCT Pub. Date: Jan. 3, 1997

[30] Foreign Application Priority Data

Jun. 14, 1995 [IL] Israel ........................................ 114140

[51] Int. Cl.[7] ............................ C12Q 1/00; G01N 33/53; A61K 38/00
[52] U.S. Cl. ............................ 435/4; 435/7.2; 435/7.21; 435/7.23; 435/29; 530/300; 530/326; 530/327
[58] Field of Search .................. 514/12–14; 530/387.9, 530/300, 326, 327; 435/29, 4, 7.2, 7.21, 7.23

[56] References Cited

U.S. PATENT DOCUMENTS 5,049,659   9/1991   Cantor et al. ............................ 530/351

OTHER PUBLICATIONS

Frandsen et al (Fibrinolysis, 6:71–76), 1992.

Hill (The Baseic Science of Oncology, Tannock et al., Eds, McGraw Hill, NY, pp. 178–195), 1992.

Burgess et al (J. Cell Bio., 111:2129–2138), 1990.

Lazar et al., (Mol Cell Biol, 8:1247–1252), 1988.

Tao et al., (J. Immunol., 142:2595–2601), 1989.

Bowie et al (Science, 247:1306–1310), 1990.

Bar–Shavit et al J. Cell Viol. vol. 123 p. 1279, 1993.

Roitt et al (Immunology, Mosby, St. Louis, pp. 6.4–6.5), 1993.

*Primary Examiner*—Susan Ungar
*Attorney, Agent, or Firm*—Oliff & Berridge, PLC

[57] ABSTRACT

The present invention concerns novel pharmaceutical compositions for the treatment of cancer, either by inhibition of the tumor metastatic tendency or alternatively by inhibiting formation of new blood vessels (angiogenesis) and thus depriving the tumor from its blood source. The active compound in the pharmaceutical compositions of the invention is a fragment of the Thrombin B-chain comprising the sequence Arg-Gly-Asp in an exposed orientation, or modified thrombin in which the naturally cryptic Arg-Gly-Asp sequence has been modified so that it is in an exposed orientation.

3 Claims, 12 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 24 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:1:

Thr Ile Thr Val Tyr Ala Val Thr Gly Arg Gly Asp Ser Pro Ala Ser
1            5                  10                15

Ser Lys Pro Ile Ser Ile Asn Tyr
            20

(2) INFORMATION FOR SEQ ID NO:2:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:2:

Ala Gly Tyr Lys Pro Asp Glu Gly Lys Arg Gly Asp Ala Cys Glu Gly
1            5                  10                15

Asp Ser Gly Gly Pro Phe Val
            20

```
(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:3:

Lys Arg Gly Asp Ala Cys Glu Gly Asp Ser Gly Gly Pro Phe Cys
1               5                   10                  15

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:4:

Ala Gly Tyr Lys Pro Asp Glu Gly Lys Arg Gly Asp Ala Cys
1               5                   10
```

METHOD FOR DETERMINING TUMOR CELL ADHESION

FIELD OF THE INVENTION

The present invention concerns anti-metastatic and anti-angiogenic pharmaceutical compositions. The compositions of the invention may be used in the treatment of cancer.

BACKGROUND OF THE INVENTION

Adhesive interactions of metastatic tumor cells with components of the extracellular matrix are required for successful target organ-colonization. The metastatic cells contact and subsequently adhere to substratum mainly via members of a family of proteins present on their membrane surface termed "integrins". A transmembrane link is established between the extracellular matrix and the cyto-skeletal cell machinery of the metastatic cell, wherein the integrin protein serves as a mediator Integrins are activated by a motif of Arg-Gly-Asp (RGD) which is common to various adhesive molecules (Albelda and Buck, *Fed. Am. Soc. Exp.*, 4:2868–80, (1990); Hynes, *Cell*, 69:11–25, (1992)).

Synthetic peptides containing the RGD motif present in short tetra-penta or hexa-sequences were found to be able to inhibit pulmonary colonization of metastatic cells (Humphries et al., *Science*, 233:467–470; (1986); Humphries et al., *Clin. Invest.* 81:782–790; (1988)). These short RGD-containing synthetic peptides were derived from the cell-binding domain of matrix molecules such as of fibronectin. It is believed that these synthetic peptides inhibit pulmonary colonization of tumor cells by acting as competitive, reversible inhibitors for the fibronectin receptor. The RGD-sequence derived from fibronectin is:

T-I-T-V-Y-A-V-T-G-R-G-D-S-P-A-S-S-K-P-I-S-I-
N-Y  (Seq. I.D. No. 3)

Other known extracellular matrix components such as vitronectin collagens, laminin, and proteoglycans, which are known to promote cell adhesion and migration, are also believed to play a role in tumor cell invasion. Synthetic peptides containing the RGD sequence are capable of competing with each of these adhesion molecules for its receptor thereby inhibiting cell attachment and migration of both normal and tumor cells on substrates coated with these adhesion molecules (Yamada, K. M. and Kennedy, D. W., *J. Cell Biochem.*, 28:99–104 (1985)); Piershbacher, M. D. and Ruoslahti, E, *Nature*, 309:30–33 (1984)).

Thrombin, the final activation product of the clotting cascade is responsible for converting fibrinogen to fibrin monomers that polymerize spontaneously to form a typical clot mesh. In addition to its major role in hemostasis, thrombin plays a role in the degradation of various constituents of extracellular matrix, induces cellular responses such as proliferation, chemotaxis as well as diverse cellular bioregulatory functions connected with wound healing and inflammation. Amino acid analysis of the thrombin B-chains reveals the presence of an Arg-Gly-Asp sequence at residues 187–189. The sequence adjacent to the RGD thrombin site being.

A-G-Y-K-P-D-E-G-K-R-G-D-A-C-E-G-D-S-G-G-P-
F-V  (Seq. I.D. No. 4)

However, although this sequence is identical to the RGD motif of various adhesion molecules, native thrombin does not exhibit adhesive properties since, as evident by crystallographic analysis, the Gly-Asp residues of the RGD motif are buried within molecule (Bode et al., *EMBO J.*, 8:3467–3475 (1989)).

We have previously shown (Bar-Shavit, et al., *J. Cell Biol.*, 112(2):335–344 (1991)) that thrombin may be converted to form an adhesion molecule for endothelial cells (EC), probably after exposure of the cryptic RGD motif. This exposure can be carried out by incubation of thrombin with plasmin, by preparation of a thrombin analog ($NO_2$-α thrombin) obtained by nitration of the tyrosine residues. The adhesion of EC cell is mediated via the $\alpha,\beta_3$ receptor, present on endothelial cells' surface (Bar-Shavit, et al., supra (1991)).

Angiogenesis, the generation of new blood vessels, is a crucial factor in tumor growth and metastasis. It was shown that an angiogentic inhibitor, secreted from a primary tumor are able to reach a remote secondary tumor and as a result inhibit the secondary's tumor growth and its metastatic spread (O'Reilly et al., *Cell*, 79:315–328, (1994)). An example of another angiogenic inhibitors are thrombospondin (Tolsma et al., *Cell Biol.*, 122:497–511, (1993) and Nickoloff et al., *Am. J. Pathol.*, 144:820–828 (1994)).

Cancer research is constantly attempting to discover novel and effective compounds which may help prevent metastasis, as well as compounds which are capable of inhibiting angiogenesis both for restricting the blood supply of the primary tumor and for preventing generation of new blood vessels brought about by the colonized metastatic cells.

SUMMARY OF THE INVENTION

The present invention is based, by one of its aspects, on the surprising finding that Arg-Gly-Asp-containing fragments (hereinafter "RGD-containing fragments") of the thrombin are capable of inhibiting the formation of lung colonization of murine melanoma metastatic cells. The RGD-containing fragments of the thrombin, are about 20 times more potent, as a metastatic inhibiting agent, than prior art RGD-containing fragments of other proteins such as fibronectin.

The present invention is further based, by another of its aspects, on another finding that RGD-containing fragments of thrombin are capable of inhibiting angiogenesis, i.e. generation of new blood vessels.

Since metastasis represents the terminal stage of events in many tumors wherein malignant cells released from a primary tumor colonize in distant sites, and since tumor growth is known to be angiogenesis dependent, the above two findings indicate that physiologically active RGD-containing fragments of thrombin or physiologically active analogues thereof, as will be explained hereinbelow, are capable of serving as active ingredients in pharmaceutical compositions for the treatment of cancer.

Thus, the present invention provides a pharmaceutical composition for inhibiting tumor metastasis comprising a pharmaceutically acceptable carrier and as an active ingredient an effective amount of a compound selected from the group consisting of:

(i) a physiologically active fragment of the thrombin B-chain comprising the sequence Arg-Gly-Asp in an exposed orientation;

(ii) a physiologically active modified thrombin in which residues 187–189 (Arg-Gly-Asp) are in an exposed orientation; and (iii) physiologically active analogues of (i) or (ii) in which one or more amino acids, other than the sequence of Arg-Gly-Asp, have been added, deleted, replaced or chemically modified without substantially altering the tumor metastatic inhibitory properties of the parent compound.

The present invention further provides a pharmaceutical composition for inhibition of angiogenesis comprising a pharmaceutically acceptable carrier and as an active ingredient an effective amount of a compound selected from the group consisting of:

(i) a physiologically active fragment of the thrombin B-chain comprising the sequence Arg-Gly-Asp in an exposed orientation;

(ii) physiologically active modified thrombin in which residues 187–189 (Arg-Gly-Asp) are in an exposed orientation; and (iii) physiologically active analogues of (i) or (ii) in which one or more amino acids, other than the sequence of Arg-Gly-Asp, have been added, deleted, replaced or chemically modified without substantially altering the angiogenic inhibitory properties of the parent peptide or protein.

The anti-metastatic and anti-angiogenic properties of the RGD-containing thrombin fragment, the modified RGD-exposed thrombin or the physiologically active analogues thereof indicate that these compounds may be used in the treatment of cancer. The term "treatment" does not necessarily refer to a situation wherein the tumor cells are directly destroyed by the action of the active compound, but also refers to the fact that the cells may be indirectly destroyed due to reduction of blood circulation as a consequence of prevention of angiogenesis. Treatment of cancer may also mean prevention of colonization of metastatic cells, originating in a primary tumor in various target organs.

Thus the present invention further provides a pharmaceutical composition for the treatment of cancer comprising a phamaceutically acceptable carrier and as an active ingredient an effective amount of a compound selected from the group consisting of:

(i) a physiologically active fragment of the thrombin B-chain comprising the sequence Arg-Gly-Asp in an exposed orientation;

(ii) a physiologically active modified thrombin in which residues 187–189 (Arg-Gly-Asp) are in an exposed orientation; and (iii) physiologically active analogues of (i) or (ii) in which one or more amino acids, other than the sequence of Arg-Gly-Asp, have been added, deleted, replaced or chemically modified without substantially altering the tumor metastatic inhibitory properties of the parent compound.

The fragment of thrombin B-chain comprising the sequence Arg-Gly-Asp (RGD), (found in residues 187–189 of the native thrombin) should feature the RGD sequence in an exposed orientation, i.e. approachable to molecules present in the external medium and not cryptic as present in the native thrombin molecule.

Verification that the RGD is indeed in the exposed and not in the cryptic orientation can be carried out either by employing various cystallographic methods or by determining whether the antibodies, against thrombin RGD-containing site, which will be specified hereinbelow, bind to the candidate RGD-containing fragment.

Any person versed in the art will appreciate that there is a large number of possible thrombin fragments of various sizes which comply with the above condition that the RGD is an exposed orientation. Physiologically active fragments can be selected, among the multitude of possible RGD-containing thrombin B-chain fragments, according to one of the assays which will be specified hereinbelow.

Examples of fragments in accordance with the invention are:

Ala-Gly-Tyr-Lys-Pro-Asp-Glu-Gly-Lys-Arg-Gly-Asp-Ala-Cys    (Seq. I.D. No. 2)

which correspond to residues 178–191 of native thrombin (termed hereinafter "Th-1"); and Lys-Arg-Gly-Asp-Ala-Cys-Glu-Gly-Asp-Ser-Gly-Gly-Pro-Phe-Cys    (Seq. I.D. No. 1)

which correspond to residues 186–200 of native thrombin (termed hereinafter "Th-2")

A person versed in the art will further appreciate the fact that the fragments which were found to be physiologically active, may be modified by using state of the art techniques to create analogues which are different from the parent fragment by one or more amino acids which have been deleted (from non-terminal positions), added, replaced or chemically modified without substantially altering the anti-metastatic properties of the parent fragment. Physiologically active analogues of the fragments which fall under the scope of the invention are those which are active in one of the assays, which will be specified hereinbelow, in a similar range of concentrations as the parent fragment.

The fragments can be prepared by any technique known in the art such as by cleavage from native purified thrombin, by synthesis using a peptide synthesizer, by cloning an appropriate DNA sequence in a host cell, and then isolating and purifying from the host transcribed RGD-containing thrombin fragment, etc.

The active ingredient in accordance with the invention may also be modified thrombin which has been treated so that the normally cryptic RGD sequence is exposed. Examples of such treatments are: digestion with various proteases, such as trypsin, plasmin, t-PA, urokinase, etc.; nitration of tyrosine residues as disclosed in Bar-Shavit et al., ((1991) supra) especially nitration of the tyrosine residues adjacent the RGD sequence (Tyr-185); incubation of native thrombin at 37° C. is also sufficient to expose some of the RGD sequences, even without addition of proteases. Exposure of the RGD site can also be carried out by minimal protease (for example, plasmin) treatment followed by treatment with heparin or heparan sulfate (for example, glypican).

In order to determine whether the RGD in the modified thrombin is in an exposed form, it is possible to use the antibodies against the thrombin RGD-containing site as will be explained hereinbelow, or to employ various crystallographic techniques.

Physiologically active modified RGD-exposed thrombin molecules which may serve as an active ingredient in the pharmaceutical compositions of the invention are such which exhibit activity in one of the assays that will be specified below.

As explained above, in connection with the thrombin RGD-containing fragments, it should be appreciated that the physiologically active, modified RGD-exposed thrombin molecules of the invention may be altered to create analogues which differ from the parent molecules by addition, deletion, replacement or chemical modification of one or more amino acid sequences. The analogues of modified thrombin which fall under the scope of the invention are those which are such which exhibit activity in one of the assays specified below, in a similar range of concentrations as the parent protein.

Both the analogues of the thrombin fragments and the analogues of the modified RGD-exposed thrombin should contain the RGD sequence in an unaltered form.

I. Assays for Determining Compounds which are Able to Serve as Active Ingredients in Anti-metastatic Pharmaceutical Compositions of the Invention (a) Compounds which, when used as a substrate are able to distinguish between high and low metastatic cells (such as murine B16-BL6 and B16-F1 cells, respectively), so that highly metastatic cells adhere to them more strongly than low metastatic cells.

(b) Compounds which are able to inhibit adhesion of highly metastatic cells (such as B16-BL6 murine melanoma) to an appropriate substratum in a competitive manner. Appropriate substratum are for example, thrombin with exposed RGD, vitronectin, fibronogen, vWF, thrombospondin.

(c) Compounds which are able to inhibit colonization of metastatic cells when co-injected to an animal with metastatic cells, for example, B16-BL6 melanoma cells.

(d) Compounds which are able to decrease growth rate of metastatic cells such as, melanoma cells, in vitro, or in vivo. Toward this, pairs of highly metastatic cells (B16-BL6 or M21 cells) are compared for their growth rate with low metastatic cells (B16-F1 cells, M21-L cells) both in vivo and in vitro. For in vivo cell growth rate, cells ($5-1 \times 10^5$ cells/animal) are injected subcutaneously into females of athymic nude mice. The diameter of each tumor is measured with calipers at various times post injection up to 6 weeks. The calculation of each tumor as $(a^2 xb)/2$ with (a) standing for width and (b) the length of the tumor. For in vitro growth, cells are seeded into a 24-well plates in RPMI medium containing 10% FCS (Gibco Laboratories, Inc., St. Lawrence, Mass.). Cells are counted using either a hemacytometer, coulter counter or the dye uptake assay, at various times.

(e) Compounds which are able to inhibit invasion through Matrigel coated filters. The in vitro invasion is performed in the membrane invasion culture system (MICS) as described in Plantefaber, L. C. & Hynes, R. O., *Cell*, 56:281–290, (1989); Seftor, E. A., Grines, W. J., Liotta, L. A., Stetler-Stevenson, W. G., Welch, D. R., and Hendrix, M. J. C., *Melanoma Res.*, 1:43–54 (1991). Briefly, after filling the lower wells of MICS with DMEM plus 10% NuSerum (Collaborative Research), the MICS are assembled by using a polycarbonate filter containing 10 µm pores coated with Matrigel (Collaborative Research) as an intervening invasive barrier. $10^5$ cells are seeded into the upper wells (measuring 1.3 cm in diameter) in the same medium and in a randomized manner across the chamber. The chamber is then placed in a 37° C. incubator with 5% $CO_3$/95% air for 72 hours. After 72 hours, the cells recovered from beneath the membrane are counted and percentage invasion is determined compared to the total number of cells originally seeded after correcting for cell proliferation. The invasive potential of the treated cells is determined as percentage of control.

(f) Compounds active in preventing metastasis according to the metastasis assay of O'Reilly, et al., *Cell*, 79:315–328, (1994). B16 melanoma cells or Lewis Lung Carcinoma (CCL) cells, are implanted into the dorsal skin of C57CB16/J mice to form visible tumors (80–160 mm$^3$) within three days. The effect of the compounds is tested on lung metastases formed in the presence of primary tumor, or as compared to the level of metastases upon removal of the primary tumors within 13–21 days. Lung weight which correlates with total tumor burden is also measured. These experiments can be performed in SCID mice lacking both T and B lymphocytes. Histological studies of the tumor are performed as well.

II. Assays for Determining Compounds which are Able to Serve as Active Ingredients in Anti-angiogenic Pharmaceutical Compositions (a) Compounds which are able to inhibit generation of blood vessels in rings of aorta (for example, rat aorta) grown in three-dimensional gels of collagen. Type 1 collagen is prepared from the tail tendons of adult Sprague-Dawley rats. Briefly, the collagen fibers are solubilized by a slow stirring for. 48 hours at 4° C. in a sterile, 1/1000 (v/v) acetic acid solution (300 ml for 1 gr. of collagen). The resulting solution is filtered through a sterile triple gause and centrifuged at 16,000 gr for 1 hour at 4° C. The collagen matrix gel is obtained by simultaneously raising the pH and ionic strength of the collagen solution. For this purpose, seven vols. of collagen solution was quickly mixed with 1 vol. of 10×Minimum Essential Medium and 2 vols. of sodium bicarbonate (0.15 M).

Thoratic aortas are obtained from 1–2 month old SD rats sacrificed by decapitation. The aortas are immediately transferred to a Petri dish with PBS. The fibroadipose tissue around the aorta is carefully removed under a dissecting microscope and 1 mm long aortic rings are sectioned and extensively rinsed with PBS.

The collagen solution (0.2 ml) is added to each of 16 mm well and gellation was allowed for 15 mins. at 37° C. The aorta ring is transferred and positioned to the center of the gel and another 0.4 ml of the collagen solution is carefully poured on top of the ring. After the gel is formed, 0.4 ml of Serum-free Endothelial Growth Medium is added and changed every other day. After 10 days newly-formed, branching microvessels were developed from the end of resection of the aorta.

(b) Compounds which are able to inhibit tumor-induced angiogenesis as disclosed in Brooks et al., *Cell.*, 79:1157–1164, (1994):

Angiogenesis induced in the chick embryo by implanting 50 mg fragments of human tumor (Melanoma/M21-L cells or B16-B16 cell) on chorioallantoic membrane (CAM) of 10 day old embryos. After 24 hours, the embryos receive I.V. innoculation of –300 µg/100 µl of tested compounds. Control embryo receive non-relevant peptides of about the same size. CAM tissue adjacent to the tumors from embryos treated with the compounds is also analyzed.

(c) Compounds which are able to inhibit angiogenesis in the CAM assays. Angiogenesis is induced on chick CAM by a 5 mm by 5 mm Whatman filter disk saturated with Hands balanced salt solution (HBSS) (untreated) or HBSS containing recombinant bFGF (150 ng/ml) bFGF-treated and placed on the CAM of 10 day chick embryo in a region devoid of blood vessels. Candidate compounds are then applied to the CAM implanted with the bFGF treated disks and the formation of blood vessels can be monitored either by photomicroscopy or immunostaining using anti $\beta 1$ or anti $\alpha v \beta 3$ antibodies.

(d) Compounds which are able to inhibit endothelial cell (EC) proliferation. Cells are seeded on tissue culture plastic plates at a low density (1×10P3/16 mm well) in 0.5 ml DMEM containing 10% heat inactivated calf serum. Ten-20 µl of growth factor containing sample is added to some of the cultures on day 2 and 4. Five to six days after seeding, the cells are dissociated with STV and counted in a coulter counter. Alternatively, the cells exposed (3–4 hours, 37° C.) to $^3$H-thymidine (5 µci/well) and DNA synthesis is determined by measuring the radioactivity incorporated into TCA-insoluble material.

In other experiments, the EC are seeded at a clonal density (300 cells/35 mm dish) and cell colonies are fixed and stained with 0.1% crystal violet, 7–12 days after seeding (Vlodavsky, I., et a., *Proc. Natl. Acad. Sci.*, USA, 84:2292–2296 (1987)).

Compounds which are active in at least one of the assays of I above may be used as active ingredients in anti-metastatic pharmaceutical compositions together with pharmaceutically acceptable carriers; may be used by themselves as anti-metastatic agents; may be used in the preparation of anti-metastatic medicaments, or used in methods of inhibiting metastatic formation by administration to the body of a subject in need of such treatment.

These compounds may be used in combination with other anti metastatic compositions such as heparin, or fragmin-heparan sulfate derived fragment, etc., or, as a complementary treatment, in conjunction with radiation, chemotherapy, intended to damage the primary tumor, or as a post-operative treatment after surgical removal of the primary tumor.

Compounds which are active in at least one of the assays of II above may be used as active ingredients in anti-angiogenic pharmaceutical compositions; may be used by themselves as as anti-angiogenic agents; may be used in the preparation of anti-angiogenic medicaments or used in methods of preventing angiogenesis by administering to the body of a subject in need of such treatment.

The compounds may be used to prevent angiogenesis induced by the primary tumor, so as to diminish its blood supply and eventually shrink drastically the size of the tumor due to prevention of circulation, or may be used to prevent colonization of metastatic cells for similar reasons, since angiogenesis is essential both for the expression of the primary tumor and the growth of established metastasis at distant sites.

The compounds of the invention may further be used to inhibit angiogenesis in other pathological conditions such as: diabetic retinopathy and rheumatoid arthritis.

Compounds which are active in at least one of the assays of I or at least one of the assays of II above may be used as active agents in pharmaceutical compositions for treating cancer.

The pharmaceutical compositions in accordance with the invention may include any pharmaceutically acceptable carrier known in the art for parenteral, oral aerosal or rectal administration. Where the pharmaceutical composition of the invention is used to prevent metastasis or prevent systemic angiogenesis, it may be administered systemically.

Where the pharmaceutical compositions in accordance with the invention are used to locally damage a primary tumor through prevention of angiogenesis, or used to prevent metastasis in a specific tissue or organ such as in the lungs, the compositions may be administered locally, for example, by direct injection to the desired site, by inhalation of an aerosol carrying particles loaded with the composition, by administration by a vehicle (such a carrier, for example, plasmid containing a specific antibody or receptor) capable of specifically targeting to the desired tissue or the desired tumor location, etc.

It may be at times desirable to use peptidomimetics in order to create analogues of the compounds of the invention which are more resistable to degradation such as cyclic peptides.

The present invention further concerns antibodies capable of specifically recognizing the thrombin RGD-containing site in an exposed orientation. Such antibodies are prepared by immunizing an animal with one thrombin RGD-fragments, for example, Th-1 and/or Th-2. Antibodies produced by the animal are then screened for those which bind specifically to the thrombin RGD-containing site in an exposed orientation and do not bind to RGD-containing sites of other molecules such as laminin, fibronectin, etc., and do not bind to native thrombin in which the RGD sequence is cryptic.

The antibodies of the invention are used as a first step in screening possible candidates for serving as active ingredients in the pharmaceutical compositions of the invention in order to select only those candidates featuring RGD sequences in an exposed orientation.

By another aspect the present invention provides a method for determining the metastatic potential of a tumor, and thus the prognosis of the cancer. Most preferably the present invention concerns a method for determining the metastatic potential of melanoma.

According to the experimental results it was found that high metastatic melanoma cancer cells have a higher level of adherence to the compounds of the invention than low metastatic cancer cells. This finding enables predicting whether a specific tumor has a high or low metastatic tendency and thus enables to choose a suitable course of treatment for the patient.

Thus the present invention provides a method for determining the metastatic tendency of a tumor comprising:
(a) incubating cells of the tumor, under conditions allowing cell adherence with a compound selected from the group consisting of:
   (i) a physiologically active fragment of the thrombin B-chain comprising the sequence Arg-Gly-Asp in an exposed orientation;
   (ii) a physiologically active modified thrombin in which residues 187–189 (Arg-Gly-Asp) are in an exposed orientation; and
   (iii) physiologically active analogues of (i) or (ii) in which one or more amino acids, other than the sequence of Arg-Gly-Asp, have been added, deleted, replaced or chemically modified without substantially altering the tumor metastatic inhibitory properties of the parent compound.
(b) determining the level of adherence of the cells to said compound, a high level of adherence indicating a high metastatic tendency and a low level of adherence indicating a low metastatic tendency.

Determination of the level of adherence can be carried out by comparing said level to a level of adherence of the tumor cells to a non-specific substrate such as bovine serum albumin (BSA). A significantly higher level of adherence than control is indicative of a high metastatic tendency of the tumor cells.

In the following, the invention will be illustrated with reference to some non-limiting drawings and examples.

DESCRIPTION OF SPECIFIC EMBODIMENTS

I. Experimental Procedures

A. Materials

Figure 1:
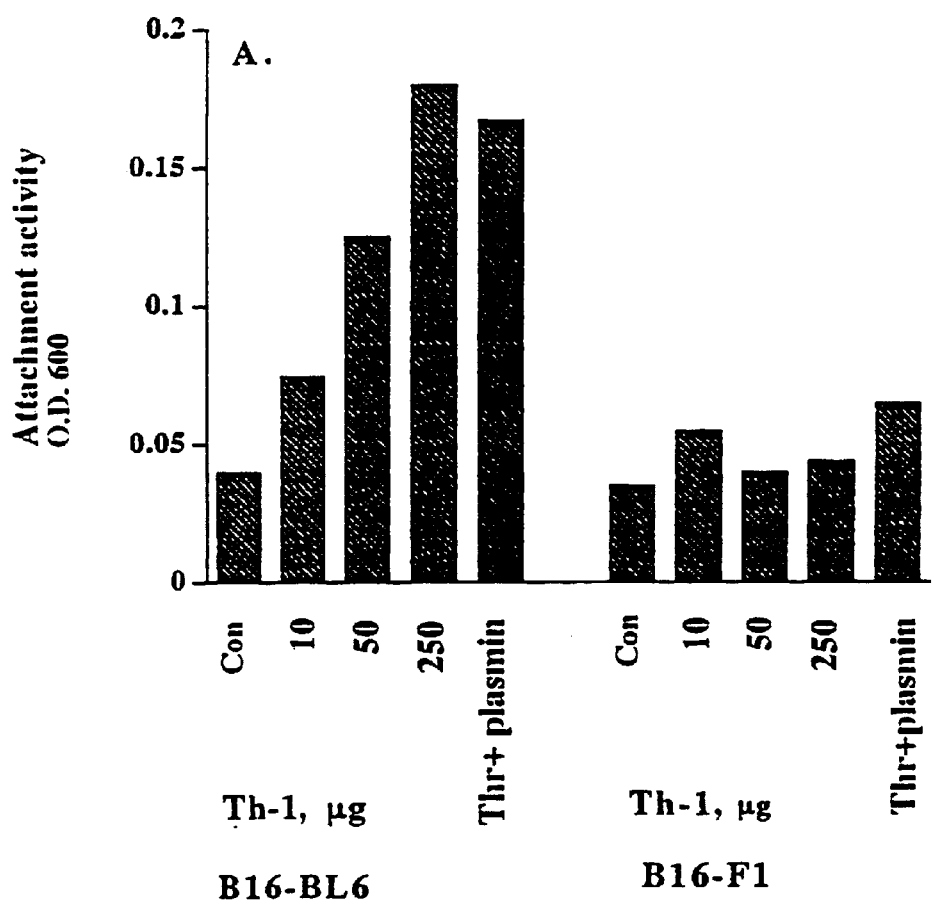
FIG. 1 shows adhesion of high (B16-BL-6-[left]) and low (B16-F1-[right]) metastatic murine melanoma cells to 10, 50, 250 $\mu$g of Th-1 or to modified RGD-exposed thrombin.

Plasmin was purchased from American Diagnostica Inc. (U.S.A.). Tissue culture dishes were obtained from Falcon Labware Division, Becton Dickinson & Co. (U.S.A.), 4-well plates were from Nunc (Denmark) and 96 well plates from Costar Co. (U.S.A.). Dulbecco's Modified Eagle's Medium (DMEM, 1 g glucose/liter, or 4.5 g glucose/liter), calf serum, fetal calf serum (FCS), penicillin, streptomycin and saline containing 0.05% trypsin, 0.01 M sodium phosphate and 0.02 EDTA (STV), were obtained from Biological Industries (Beit Haemek, Israel). The synthetic hexapeptides (GRGDSP, GRGESP) were obtained from Peninsula Laboratories, Inc. (U.S.A.). All other chemicals were of reagent grade, purchased from Sigma (U.S.A.).

B. Preparation of Cells

The murine melanoma cells B16-BL6 and B16-F1 (provided by Dr. I. J. Fidler, The University Texas, M.D. Anderson Cancer Center, Houston, Tex.), selected, for high- and low-lung colonization potential according to the procedure disclosed in Fidler, I. J., Selection of successive tumor lines of metastasis, *Nat. New Biol.* (Lond) 292:148–149 (1973) were maintained as adherent monolayers in DMEM supplemented with 10% FCS.

Cloned populations of adult bovine aortic endothelial cells (EC) were established as previously described (Gospodarowicz et al., *PNAS*, 73:4120–4124 (1976). Cells were cultured in DMEM (1 g glucose/liter) containing 10% bovine calf serum (BCS), penicillin (50 U/ml) and streptomycin (50 µg/ml) at 37° C., in 10% $CO_2$ humidified incubators. Partially purified, brain derived basic-fibroblast growth factor (bFGF) (100 ng/ml) was added to ECs, every other day during the phase of active cell growth for about 10–14 days. Cells were dissociated with 0.05% trypsin/0.02% EDTA, 0.0 M sodium phosphate (pH 7.4) STV and subcultured at a split ratio 1:5.

ECs were characterized by indirect immunofluorescence using rabbit anti-human factor VIII antibodies (Bchringwerke Ag, Germany). Cultures were routinely tested for microbial infection and were verified to be mycoplasma-free. Cells were detached for 2 min. with 0.02% EDTA and resuspended carefully to $5.0–7.5\times10^5$ cells/ml in DMEM.

Human melanoma cells (kindly provided by Dr. P. Brodt, McGill University, Montreal, Quebec, Canada), maintained in RPMI-1640 medium supplemented with 10% FCS. Selection for high metastatic melanoma cells were as described (Nip, J., Shibata, H., Loskutoff, D., Cheresh, D. and Brodt, P., *J. Clin. Invest.* 90:1406–1413 (1992); Nip J., Rabbani S., Shibata, H. R. and Brodt P., *J. Clin. Invest.* 95:2096–2103, 1995)).

C. Animals

6–10 week old specific, pathogen-free, inbred female of C57BL/6 mice were used. Care and use of animals were—in accordance with institutional guidelines.

D. Induction of Lung Metastasis $1\times10^5$ cells/0.2 ml/mouse B16-BL6 cells were injected into the lateral tail vein of unanesthetized C57BL/6 mice. The mice were monitored on a daily basis and sacrificed 2 weeks later by cervical dislocation. The animals were necropsied, and the lungs were removed, washed in water, and fixed in Bouin's solution (containing saturated solution of picric acid, 2% glacial acetic acid and 3% formaldehyde). The number of lung nodules was determined under a dissecting microscope.

The liver, kidney, spleen, lymph nodes and pancreas were also examined for presence of melanoma nodules (Esumi et al., *Cancer Res.*, 51:4549–4556, (1991).

E. Determination of Attachment of Endothelial Cells

Confluent endothelial cells were dissociated with trypsin-EDTA solution, washed once in growth medium and resuspended in DMEM containing 0.2% bovine serum albumin (BSA). $1.3\times10^5$ cells/well/0.2 ml DMEM containing 0.2 BSA were added to each protein-coated well and incubated at 37° C. for 2 h. The plates were then washed three times with phosphate batter saline (PBS) and the firmly attached cells were fixed with 3% paraformaldehyde.

Fixed cells were then rinsed with 0.1 M borate buffer (pH 8.5), stained for 10 mins. at 22° C. with 0.1 ml/well methylene blue (1% in 0.1 M borate buffer, pH 8.5) and washed four times in borate buffer. This procedure removed practically all non cell-bound dye. Methylene blue which was incorporated by cells was dissolved with 0.1 N HCl (0.2 ml/well) for 40 mins. at 37° C., and determined by its absorbance at 600 nm.

It is known that uptake of methylene blue is linearly correlated to the number of viable cells (Goldman and Bar-Shavit, *J. Natl. Cancer Inst.*, 63:1004–1016, 1979). Each experiment was performed at least 3 times and the variation between different experiments did not exceed ±20%.

F. Peptide Synthesis

Peptides representing different regions of thrombin B-chain, such as 177–190 and 367–380, were synthesized by the peptide synthesis core-unit of the Hebrew University Medical School using a peptide synthesizer (Applied Biosystems, Model 430, division of Perkin Hemler Inc.). One step of FPLC purification was performed, to purify the products of the synthesizer.

G. Production and Purification of Anti-thrombin-RGD Antibodies

Rabbit anti-thrombin-RGD antibodies were obtained according to state of the art procedures. In brief, rabbit anti-thrombin-RGD antiserum was obtained following subcutaneous injections of the synthetic peptide Th-1 representing the 14-amino acid residues 177–190 of thrombin B-chain. The antibodies in the IgG fraction, obtained by 50% ammonium sulfate precipitation and DEAE chromatography, recognized in a radioimmunoassay the 14 amino-acid peptide ($ED_{50}$=2 ng/ml), but did not recognize native thrombin, prothrombin, fibrinogen, or fibronectin, as a concentration of up to 0.4 µg/ml.

H. ELISA 96-well microtiter plates were coated by 5 µg/ml of Th-1 or by fibronectin, fibrinogen, vitronectin, thrombin or prothrombin 5 µl/ml in buffer pH 8.0, by incubation at 4° C. for 4 hours. The unbound material was washed away and the surface of the microtiter wells was saturated with 5% dry milk in TTBS (50 mM Tris pH 75, 150 mM NaCl and 0.1% Tween-20) by incubation at 24% for 1 hour. The wells were washed with 0.5% dry milk in TTBS 3 times, and then incubated for 2–16 hours at 24° C. with various dilutions of the test antiserum, followed by 3 washes and a sequential incubation, at 24° C. for 1 hour, with alkaline phosphatase conjugated anti-rabbit antibodies (Promega, U.S.A.) added at a dilution of 1:50000. The wells were then washed three times performed and substrate nitrophenyl phosphate (PNPP) in diethanolamine buffer was added. Color development was determined by measuring the optical density at 405 nm.

I. Immunohistochemistry Procedure

Frozen sections of human arterial tissue were surgically removed by carotid endartectomy from the bifurcation of the carotid artery. 5 µM thick sections were permeabilized by incubation with 2 µg/ml proteinase K at 37° C. for 15 mins. and washed in PBS. Endogenous peroxidase activity was quenched by incubation with 0.3% $H_2O_2$ in PBS followed by three PBS washes. Sections were incubated with purified rabbit-antiserum against Th-1, prepared as described in I(G) and diluted in 5% goat serum in PBS. Antibody binding was detected by sequential incubations of the sections with biotinylated goat anti-rabbit serum and strepavidin-peroxidase complex (Bio-Makor, Israel). Positive staining was detected by substrate reaction with diamino benzidine. Sections were counterstained with hematoxylin and mounted in Permount (Fisher).

II. Adhesion of High and Low Metastatic Melanoma Cells to Th-1 Peptide

B. Method

Tissue culture plates were coated with either 10, 50 or 250 µg/well of Th-1; with 10 µg/ml of thrombin digested by incubation at 22° C. for 1 hour with plasmin (2 µg/ml); or with 0.2% BSA which served as control (CON). $0.5 \times 10^6$ cells/wells of B16-BL6 or B16-F1 cells, which are known to present in vivo high and low pulmonary colonization, respectively, were incubated at 37° C. for 2 hours with the plates coated with the substrates described above. The plates were then washed 3 times with phosphate buffer saline (PBS) and the attached cells were fix by 3% formaldehyde.

The level of cell attachment was evaluated by the methylene blue uptake assay described in I(E) above. The variation between triplicate determinations did not exceed ±12% of the mean.

As an additional control served as a substrate to 14-amino acid peptides representing residues 367–380 of thrombin B-chain (not containing the RGD sequence).

B. Results

FIG. 1 shows a high, dose dependent adhesion of the highly metastatic B16-BL6 cells to the Th-1 peptide as compared to the low relatively dose independent adhesion level of B16-F1 cells under the same conditions. B16-BL6 cells adhered in a similar manner to thrombin digested with plasmin, as compared to very low or complete absence of adhesion obtained by the low metastatic B16-F1 cells.

No adhesion was observed to the 14 amino acid peptides of residues 367–380 of thrombin B-chain (data not shown).

III. Similar Inhibition of Adhesion of B16-BL6 Melanoma Cells to Substratum by Th-1 Peptide Method A. Method 10 µg/ml of thrombin was digested with 2 µg/ml plasmin by incubation in 22° C. for 1 hour. Tissue culture plates were coated with digested plasmin by incubation at 4° C. for 2 hours.

$1 \times 10^6$ B16-BL6 cells were incubated, at 22° C. for 30 mins. with increasing concentrations of Th-1 peptide (20–300 µg) prior to attachment to treated tissue culture plates by incubation at 37° C. for 2 hours. The attached cells were washed 3 times with PBS and fix with 3% formaldehyde. The level of attachment was evaluated by the methylene blue uptake assay described in I(E) above. The variation between triplicate determination did not exceed ±15% of the mean.

B. Results

Figure 2:
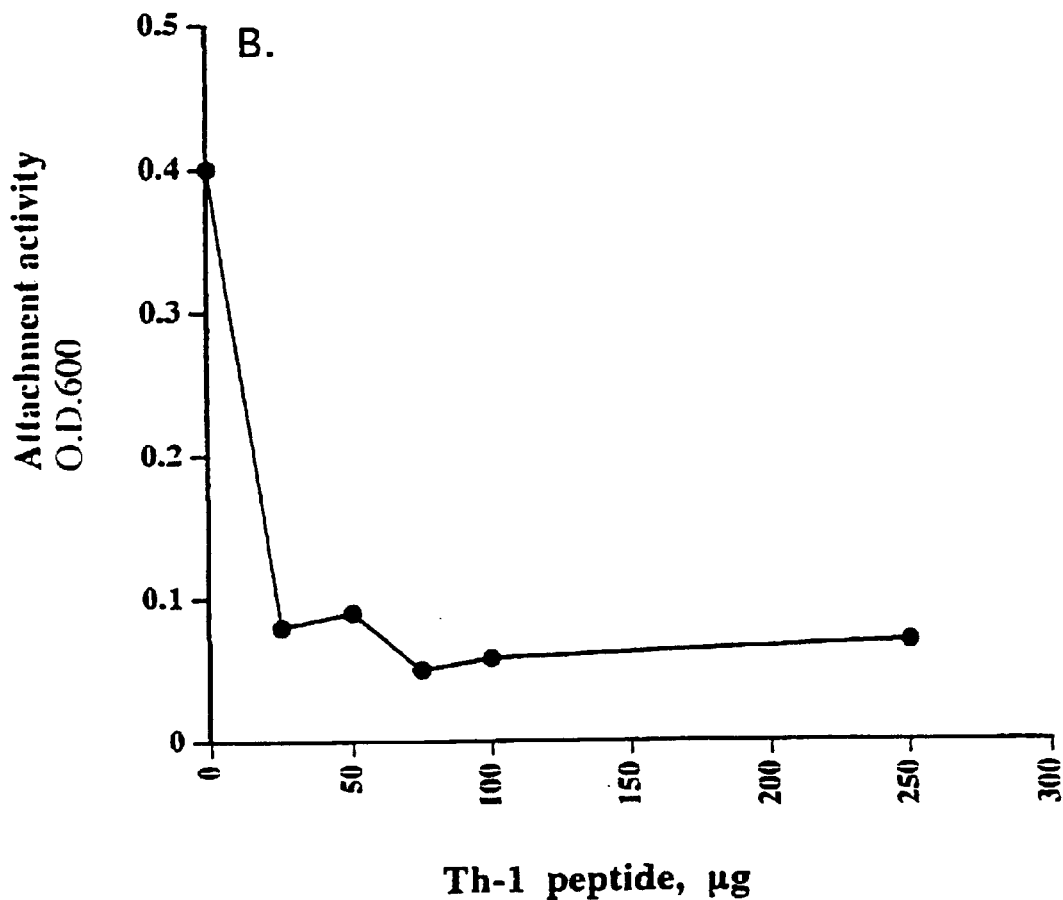
FIG. 2 shows inhibition of B16-BL6 murine melanoma cell adhesion to modified RGD-exposed thrombin by varying concentrations of Th-1.

FIG. 2 shows that Th-1 peptide inhibited, in a dose depended manner, the adhesion of B16-BL5 cells to modified RGD-exposed thrombin produced by digestion with plasmin (Bar-Shavit, supra (1991)).

The results in II(B) and III(B) above indicate that the Th-1 peptide is physiologically active and able to distinguish between highly metastatic and low metastatic melanoma cells. Furthermore, these results indicate that Th-1 is able to directly compete with modified RGD-exposed thrombin for binding to cell-surface receptors. Inhibition of adhesion to the substrate (modified RGD-exposed thrombin) was obtained already at a concentration of 16 µM.

Similar results were obtained with the Th-2 peptide.

IV. Inhibition of Lung Colonization by Th-1 Peptide

A. Method

B16-BL6 cell monolayers in culture were detached for 2 mins. with 0.02% EDTA and resuspended gently to $1 \times 10^5$ cells/0.2 ml DMEM. 0.5 mg/$1 \times 10^5$ cells/0.2 ml of Th-1 was preincubated, at 37° C. for 30 mins, with a half of the cells' cultures prior to injecting mice. A single cell suspension ($1 \times 10^5$ cells/0.2 ml/mouse), comprising either Th-1 treated or Th-1 untreated melanoma cells was injected slowly into the lateral tail vein of C57BL/6 mice.

Fourteen days after injection, the mice were sacrificed, and their lungs were excised and fixed with 10% formaldehyde and stained with saturated picric acid. The number of surface melanoma colonies was counted visually or with the aid of a dissecting microscope.

B. Results

Figure 3:
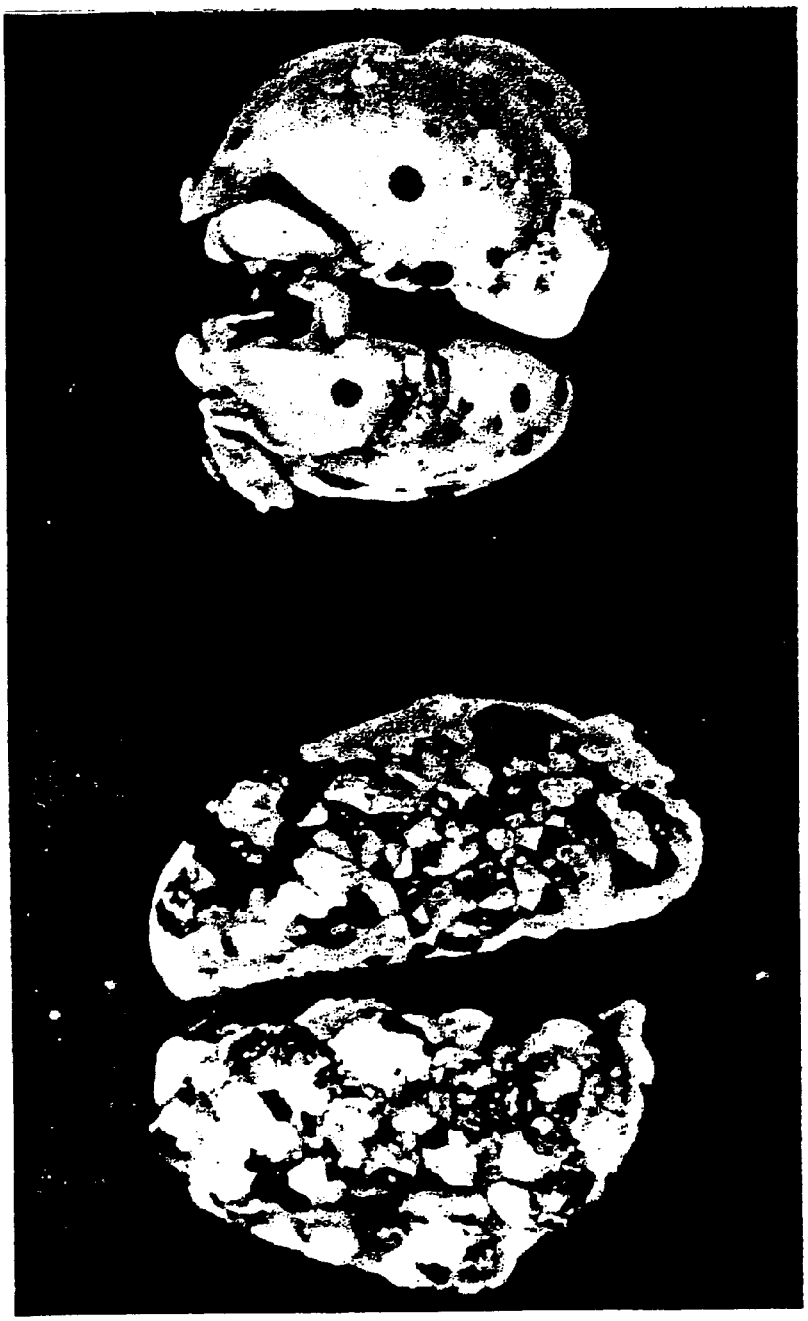
FIG. 3 shows dissecting pictures (1:100) of lungs of mice injected with B16-BL6 melanoma cells alone (right) or of lungs of mice co-injected with B16-BL6 melanoma cells at Th-1.

As can be sen in FIG. 3, co-injection of Th-1 peptide with B16-BL6 murine melanoma cells resulted in marked reduction of melanotic colonies detected in the lungs, 14 days after injection, as compared with injection of B16-BL6 alone.

Over 90% inhibition was obtained at a concentration of 0.5 mg peptide/mouse, as compared to inhibition of metastasis by the GRGDS pentapeptide exhibiting the fibronectin RGD-site disclosed by (Humphries et al. supra (1988) which inhibition was evident only at concentration of 3 mg/mouse.

Therefore it is clearly evident that the Th-1 peptide is about 20 fold more potent than the GRGDS peptide of prior art in inhibiting metastasis of melanoma cells.

Injection of control peptides corresponding to region 367–380 of thrombin B-chain (not containing the RGD-site) or a tetradecapeptide of Th-1 with one altered amino acid in the RGD sequence (D residue altered to E residue) did not affect the extent of melanoma lung colonization under the same conditions (data not shown). These results emphasize the specificity of the RGD-containing peptide and emphasize the fact that the RGD sequence is essential to the physiological activity and should not be altered.

V. Adhesion of High and Low Metastatic Human Melanoma Cells 61, MIM8 and MeWo, Respectively, to Th-1

Human melanoma cells established from lymph node metastases, being either MeWo cell lines representing diverse metastatic potentials, or a highly metastatic cell line originating from a melanoma patient (Nip et al., *J. Clin. Invest.* 90:1406–1413 (1992)) were used. High metastatic cells were selected by adhesion to lymph nodes and were designated as MeWoLN161 (also referred to as "61").

The cells were incubated with 100 $\mu$g/ml Th-1 and their adherence was determined as described above. As control, the level of adherence of the cells to BSA coated substrate was determined.

Figure 4:
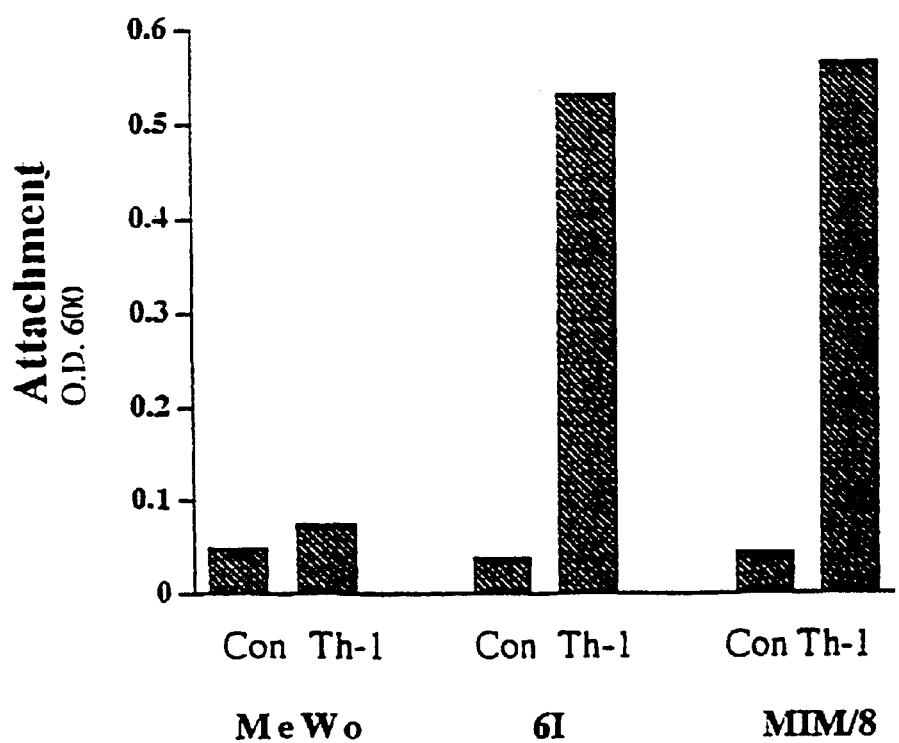
FIG. 4 shows adhesion of high (61 and MIM/8) and low (McWo) metastatic human melanoma cell lines to Th-1 (Con-adhesion to BSA coated substrate)

As can be seen in FIG. 4, both 61 and MIM/8, which are high metastatic cells, show a significantly higher level of adherence to Th-1 as compared to control, than the low metastatic melanoma cells MeWo.

VI. Characterization of Antibodies Directed Against the RGD-site of Thrombin in Exposed Orientation Method 5 $\mu$g/ml thrombin (□), thrombin digested with 2 $\mu$g/ml plasmin (▲), 5 $\mu$g/ml Th-1 (○), 5 $\mu$g/ml prothrombin (♦) were used to coat ELISA plates, followed by incubation, at 24° C. for 1 hour with various dilutions of anti-thrombin RGD antibodies directed against the RGD-containing residues 187–190. Detection of specifically bound antibodies was performed by sequential incubations with alkaline phosphatase conjugated anti rabbit-IgG (Promega, U.S.A., dilution 1:5000) and the appropriate substrates, according to the manufacture instructions.

Results

Figure 5:
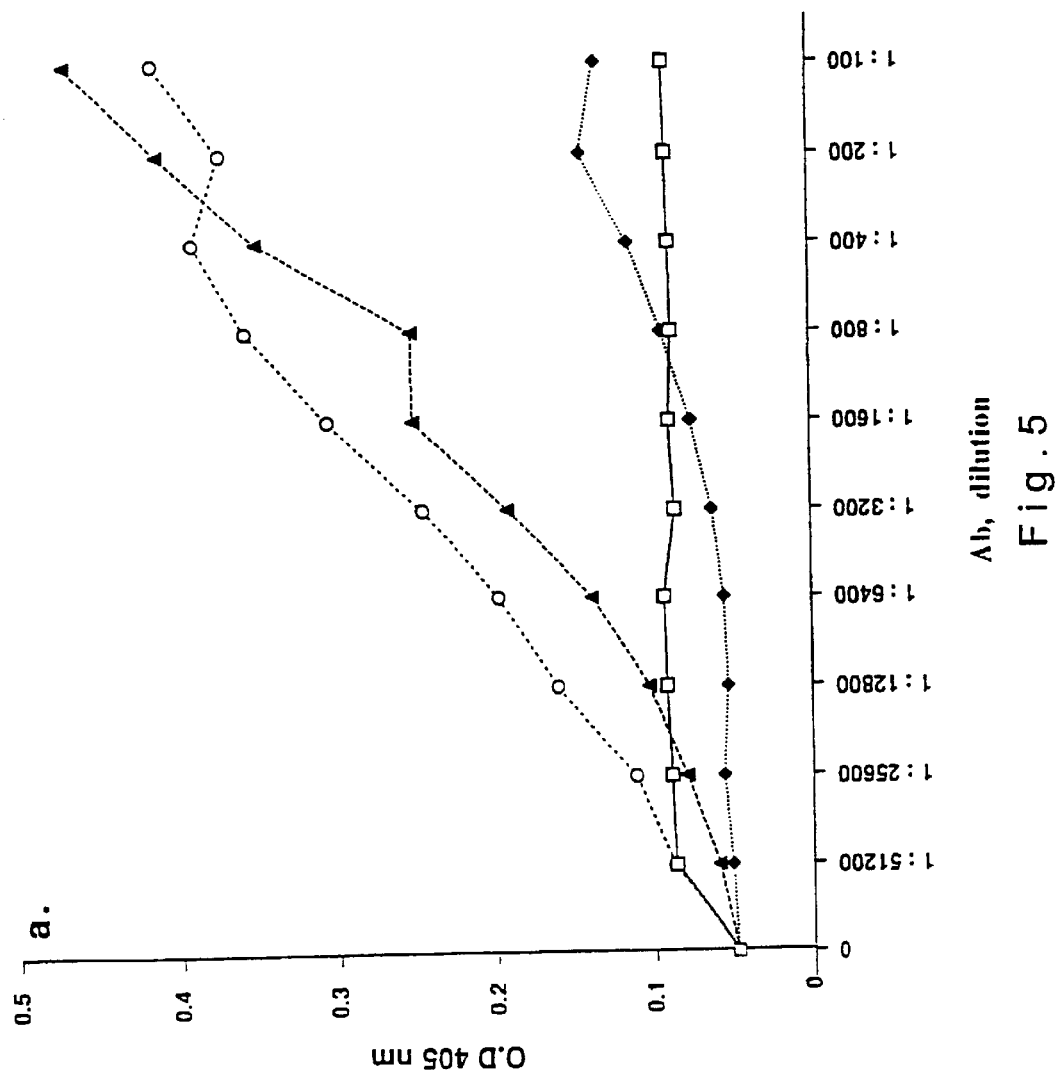
FIG. 5 shows binding of the antibodies of the invention, as determined by ELISA, to thrombin (□), modified RGD-exposed thrombin (▲), Th-1 (○), prothrombin (♦)

As can be seen in FIG. 5, antibodies prepared as described in I(G) above were able to specifically bind and recognize prothrombin, Th-1 and plasmin treated thrombin, which all feature exposed RGD-sites (Bar-Shavit et al., supra) but not bind to untreated thrombin or prothrombin where the RGD site is unexposed.

Figure 6:
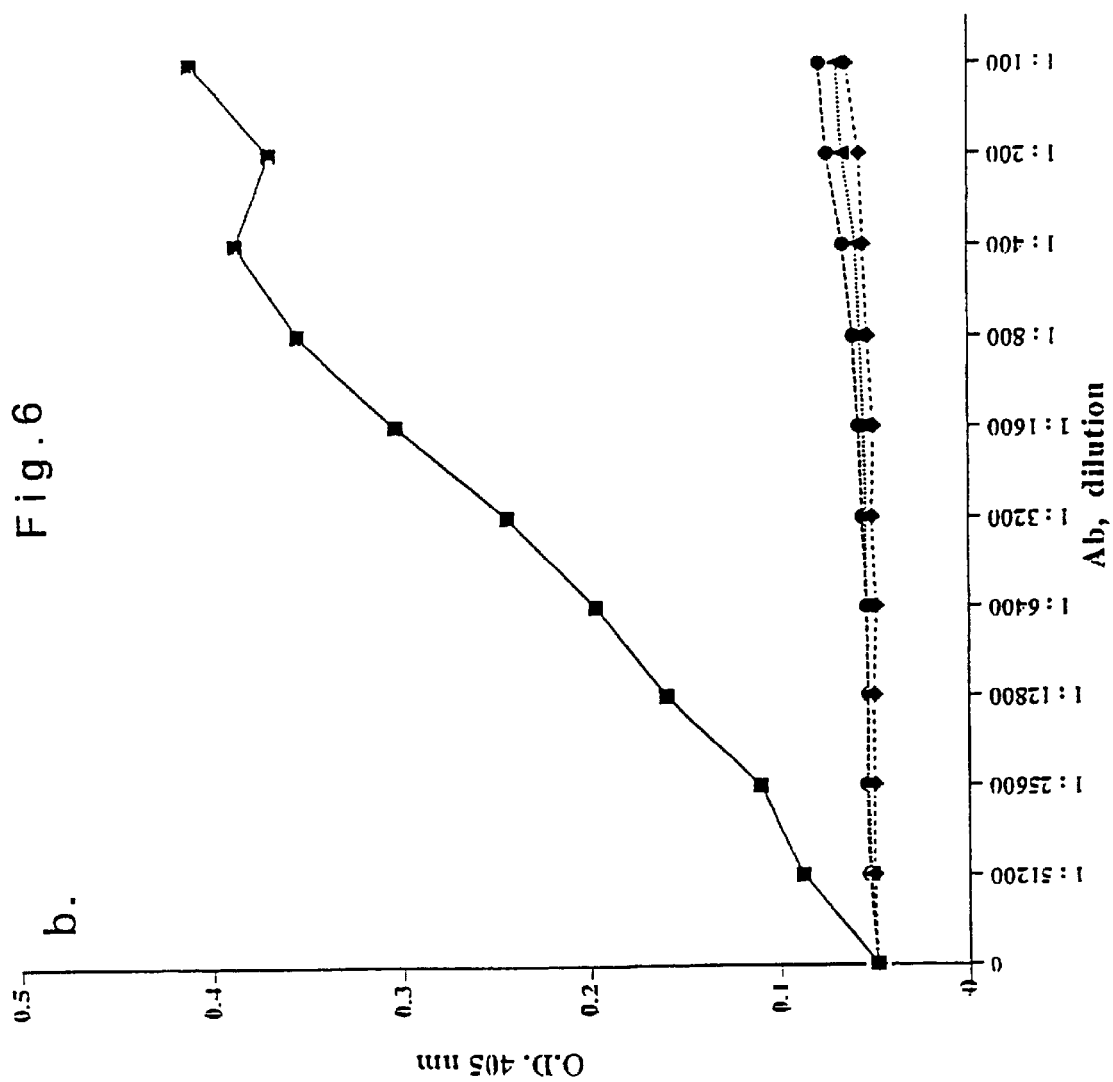
FIG. 6 shows binding of the antibodies of the invention, as determined by ELISA, to Th-1 (■), fibronectin (♦), fibrinogen (●), and vitronectin (▲)

FIG. 6 shows that the antibodies of the invention specifically recognize the RGD-exposed site of thrombin but are unable to bind to the RGD motif present in other molecules such as fibronectin, fibrinogen or vitronectin.

Figure 7:
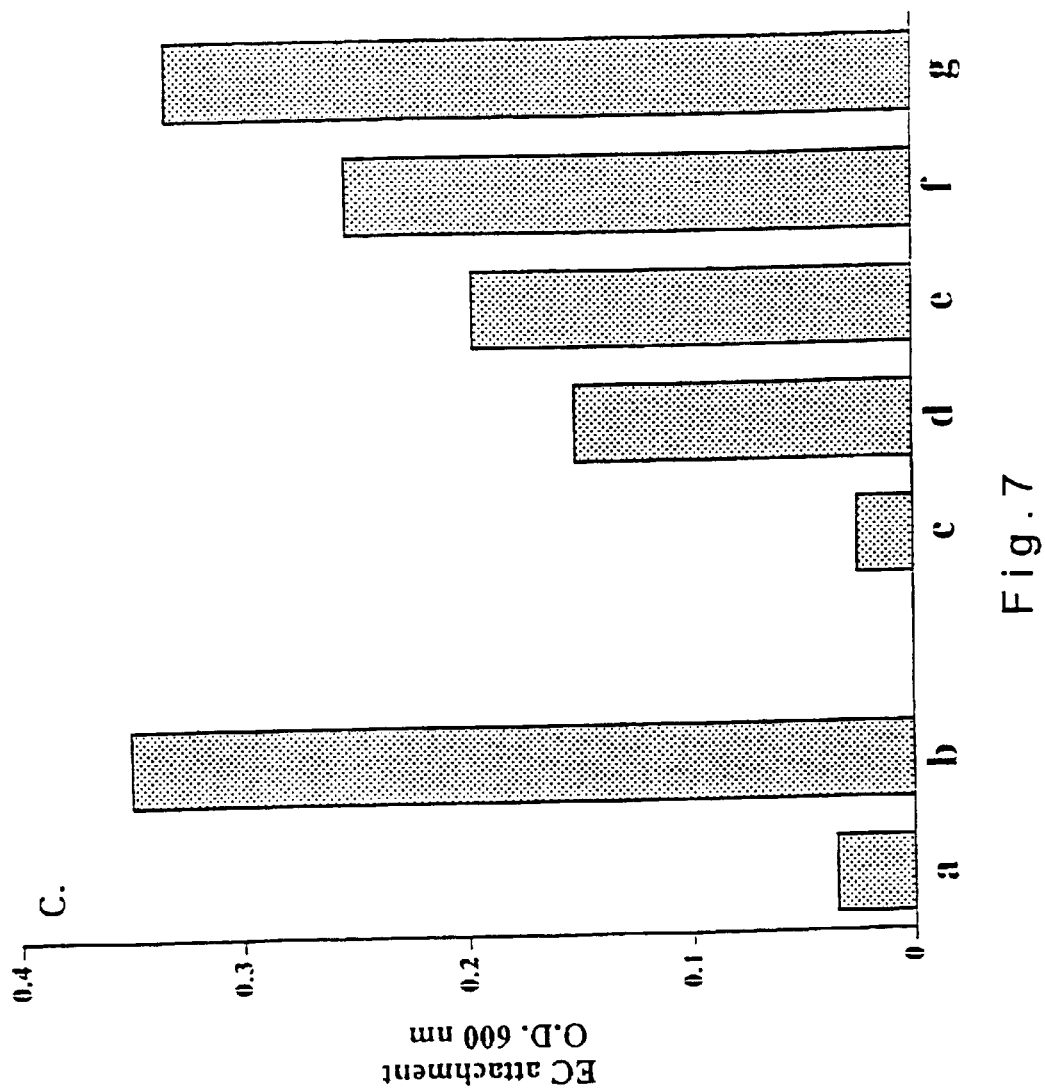
FIG. 7 shows the inhibition of adhesion of B16-BL6 murine melanoma cells to substratum by the anti-thrombin RGD antibodies of the invention of various dilutions: 1:50 (c); 1:100 (d); 1:200 (e); 1:400 (f); 1:800 (g). The level of adhesion of endothelial cells to a substratum of modified RGD-exposed thrombin is shown in (b) as compared to non-coated control (a)

FIG. 7 shows inhibition of adhesion of endothelial cells to a substratum of modified, RGD-exposed thrombin in a dose dependent manner by these antibodies. Similar results of selective inhibition of adhesion to thrombin RGD by these antibodies were obtained also for B16 murine melanoma cells (data not shown). Adhesion of cells was performed in the presence ([c–g] showing adherence of melanoma cells) or absence ([a,b] showing adherence of endothelial cells) of anti RGD-exposed thrombin antibodies, and FIG. 7(*a*) shows adhesion of endothelial cells to non-coated plates. FIG. 7(*c–g*) show adhesion in the presence of various dilution of antibody.

These results clearly indicate that the antibodies of the invention are capable of selectively recognizing thrombin and neutralizing its adhesion promoting activity. The fact that they are specifically capable of recognizing the RGD-exposed site in thrombin was demonstrated by their failure to recognize the site in other adhesive RGD-containing proteins such as fibronectin (FIG. 6), fibrinogen and vitronectin (data not shown) as well as their failure to recognize the cryptic RGD-site in native thrombin.

Similar results were also obtained using the Th-2 peptide.

VII. Immunostaining of Human Vessel Wall Sections

Method

Immunohistochemical staining of frozen sections of carotid artery with anti thrombin-RGD antibodies (A—dilution of 1:100, D—dilution of 1:200) using the peroxidase-avidin-biotin detection system was carried out. Sections were also stained in the absence of anti RGD-thrombin antibodies with (C) or without (B) specific Movat staining, specific for illustrating the different layers in the vessel wall. One can clearly note the different layer distribution as demonstrated by Movat staining showing the relatively thick neointima formed and a clear line of the internal elastic lamina (FIG. 8C).

Results

Figure 8:
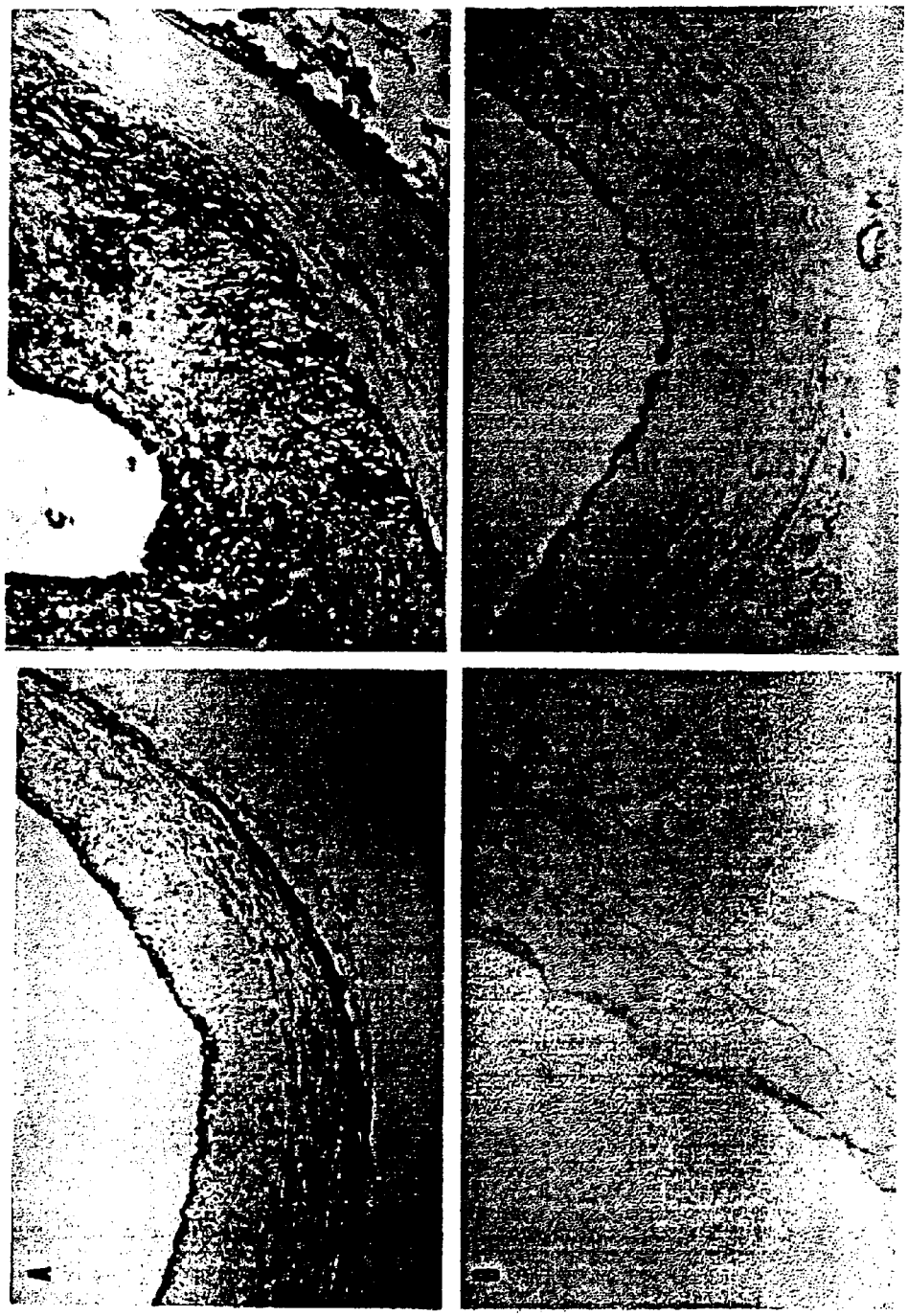
FIG. 8 shows immunohistochemical staining of frozen sections of carotid artery with anti-thrombin RGD-antibodies. (A dilution 1:100, D dilution 1:200), as well as staining without anti-thrombin RGD antibodies (B), with (C) or without (A,D) specific Movat staining.

The pattern of immunohistochemical staining of blood vessels using the antibodies directed toward the exposed RGD-site in thrombin, showed abundant and specific appearance, both at the lumial surface and medial region of human carotid frozen sections (FIG. 8A, 8D). Marked staining was obtained at a dilution of 1:200 (FIG. 8D), as compared to antibody staining at 1:100 dilution (FIG. 8A). Specificity of the immunostaining was demonstrated by the failure to detect any positive staining in the absence of the antibodies (FIG. 8B). These results indicate that thrombin derived RGD containing fragments are widely distributed throughout the vascular system. In fact, it appears that these antibodies may provide a good marker for the vessel wall as noted by capillary vessel cross section at the bottom (FIG. 8D).

VIII. Angiogenic Effect of Th-1 Peptide

A. Method

An angiogenesis model of cell growth from explants of rat aorta, as disclosed in Roberto et al., *J. Cell Biol.*, 124:(1,2) 183–193 (1994); Friedlander et al., *Science*, 210:1500–1502 (1995), was used. In this system, the rings of aorta are cultured in a three-dimensional gel of collagen sprouts to microvessel. To the medium of the cultured aorta rings were added 20–100 $\mu$l/ml of Th-1 as control served a peptide of similar size from the 367–390 region of thrombin, not containing the RGD-site.

B. Results

Figure 9:
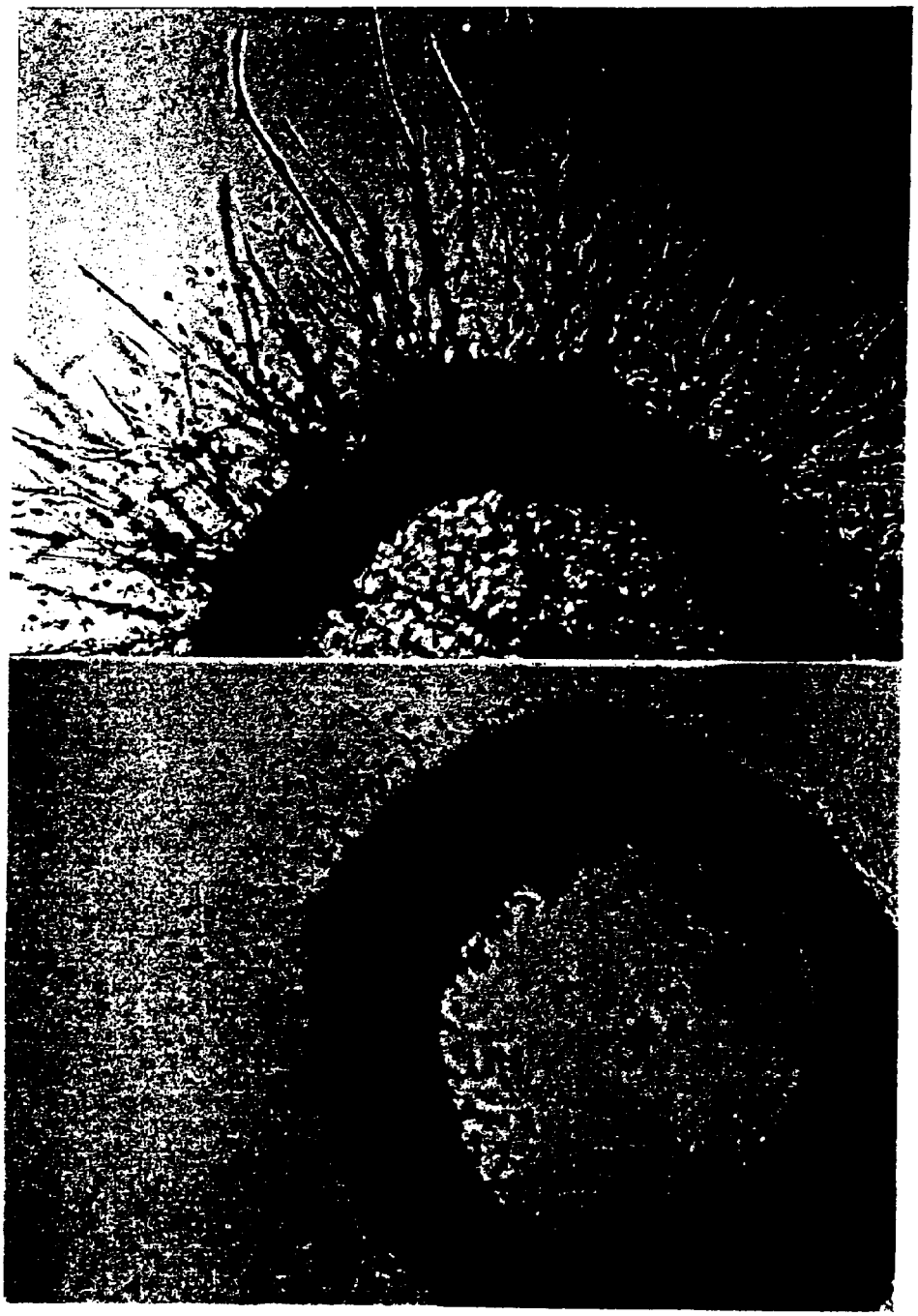
FIG. 9 shows rat aorta rings cultured in three dimensional gels of collagen in the presence of Th-1 (bottom) or in the presence of another fragment 367–390 of thrombin (top)

As can be seen in FIG. 9, 100 $\mu$g/ml concentration of Th-1 was able to inhibit angiogenesis (9B) as compared to a similar concentration of a peptide of similar size not containing the RGD-site (9A).

These results demonstrate the activity of the peptide of the invention as an anti angiogenic agent.

Figure 10:
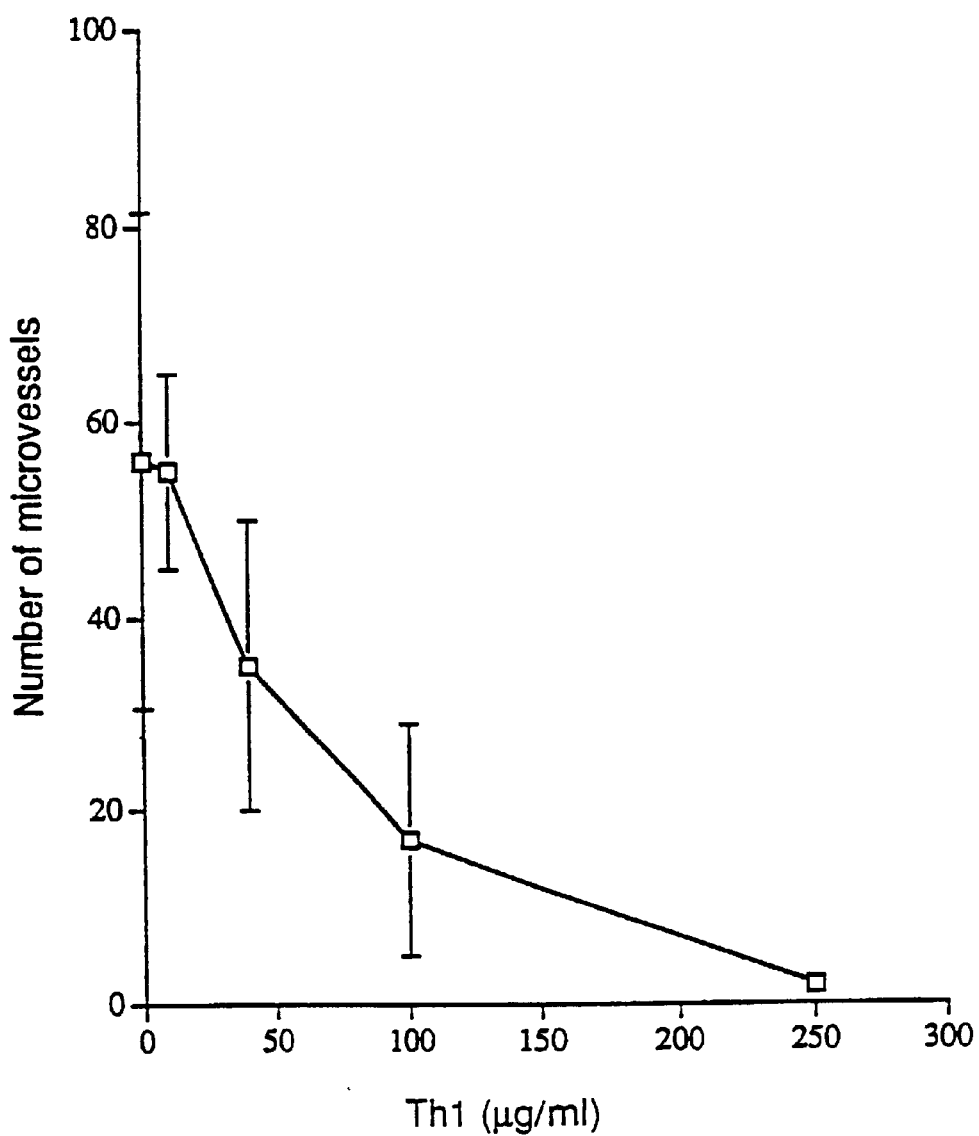
FIG. 10 shows inhibition of microvessel formation in rat aorta rings as a function of Th-1 concentration.
Figure 11:
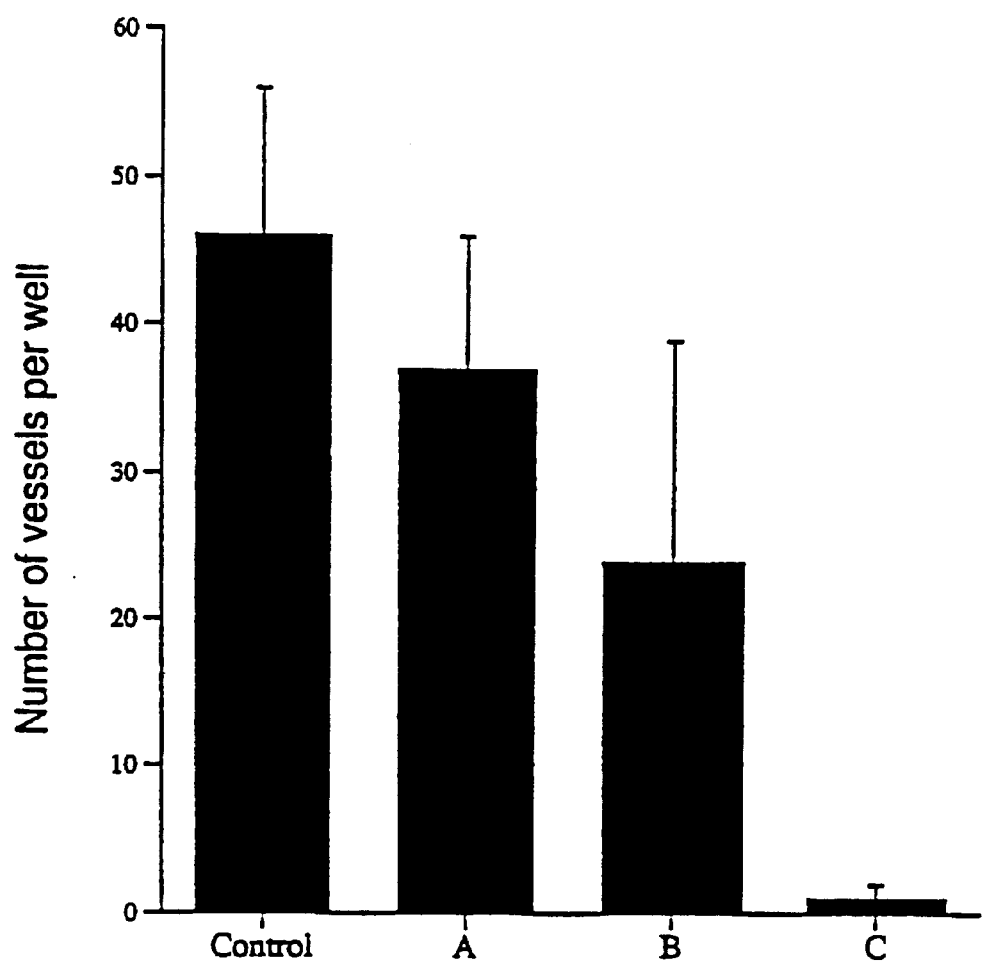
FIG. 11 shows the reversibility of Th-1 inhibition of microvessel sprout formation. Number of sprouts with no Th-1 (Control); after 2 day incubation with 150 µg/ml Th-1 and replacement of fresh medium for additional 12–14 days (A); after incubation with 150 µg/ml Th-1 for 6 days and replacement by fresh medium for additional 8 days (B); after incubation with 150 µg/ml for 14 days (C)

The above experiment was repeated with 10–250 $\mu$g/ml of Th-1 applied to the same ring system and a dose dependent inhibition in sprout formation of the microvessel was observed. As can be seen in FIG. 10, 50% inhibition of explant formation was obtained at nearly 50 μg/ml peptide. Complete inhibition was observed at 100–250 μg/ml peptide. This inhibition was not due to a toxic effect since, when a 150 μg/ml of peptide was added for a period of 48 h, then washed free of the peptide and replaced by fresh medium (for additional 14 days), nearly complete recovery of the explants was formed as was evidenced as shown in FIG. 11A. Incubation with the peptide for longer periods of time, then washed out, a further increased inhibition in the level of microvessel formation, was observed (FIG. 11B) and complete inhibition obtained when the peptic is constantly present (up to 14 days) (FIG. 11C).

Figure 12:
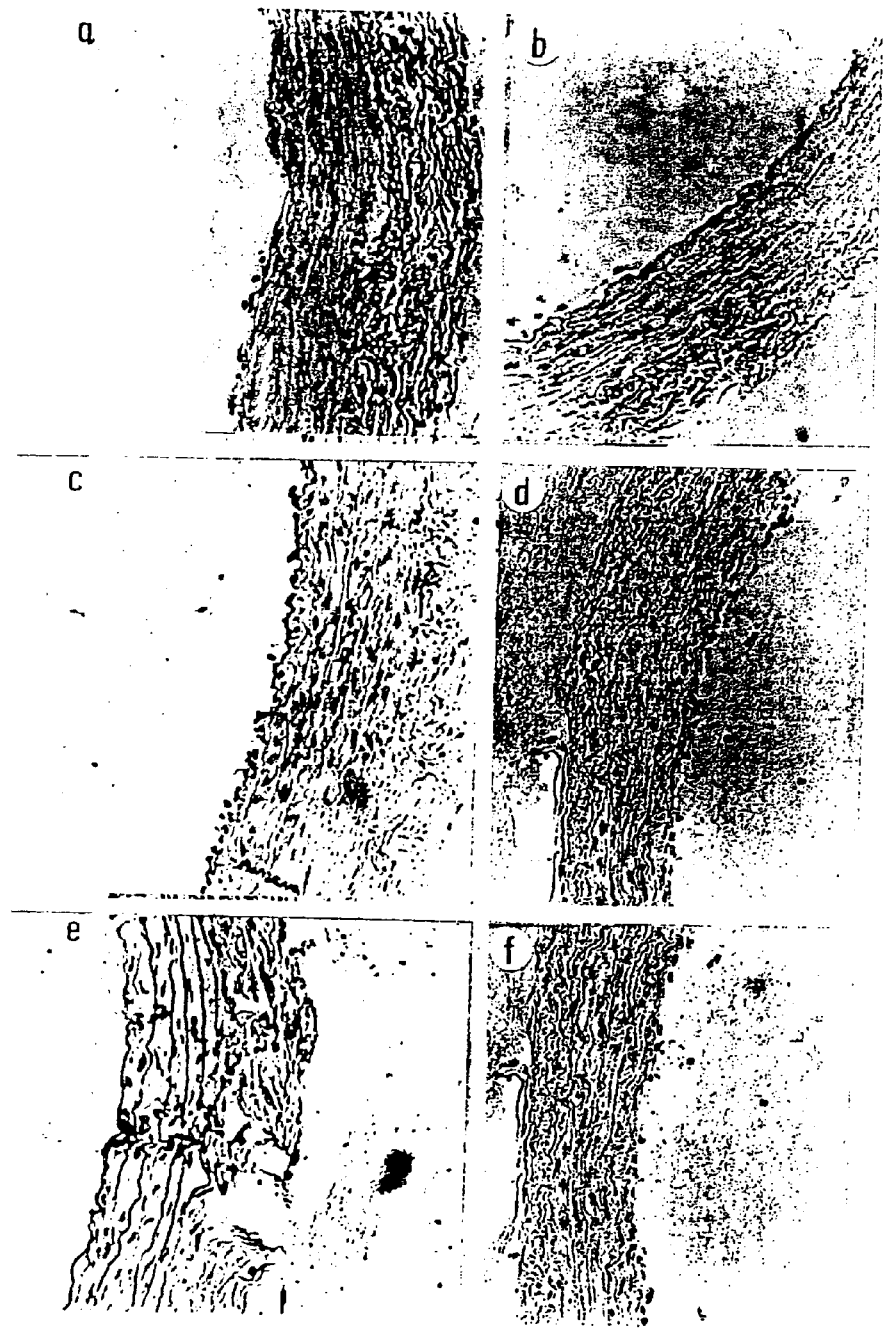
FIG. 12 shows a dose dependent apoptosis induced by Th-1 peptide. Apoptosis assayed by the TUNFI procedure, in the presence of increased concentrations of Th-1 peptide (a); control untreated rat-aorta ring (b); nuclei staining of rat aorta ring in the presence of 10 µg/ml Th-1 peptide (c); nuclei staining in the presence of 40 µg/ml Th-1 (d); Th-1 concentration of 100 µg/ml (e); total positive nuclei staining for apoptosis. This was achieved by DNase (1µ/ml) treatment of the paraffin section (f). Apoptosis induced in the presence of 250µ/ml Th-1 peptide.

Thrombin Derived-RGD Peptide Induces Apoptosis in an Angiogenesis Experimental Model, in vitro Apoptosis, or programmed cell death, can be evaluated by DNA fragmentation using a technique based on terminal deoxynucleotidyl transferase (TdT) reactivity with DNA breaks. This histochemical staining was based on the original "TUNEL" method (Gavrieli, et al., *J. Cell Biol.* 119:493–501 (1992)). Tissue was fixed in buffered formalin; after deparaffinization and hydration, the slide was quenched with $H_2O_2$, in methanol. In order to strip the nuclear proteins, the tissue was preincubated in Tris-HCl and then incubated with proteinase K (20 μg/ml) for 15 minutes and washed. DNA fragments are elongated and labeled with biotinylated poly dUTP, introduced by terminal deoxynucleotidyl transferase. Finally, bound biotin is stained by avidin conjugated peroxidase, developed with nickle-enhanced diaminobenzidine. For positive control (FIG. 12, E) staining serves a preparation that was exposed to DNase digestion (according to Gavieli, et al., supra). As can be seen in FIG. 12, apoptosis is induced by a dose dependent manner, judged by the nuclei staining. It is important to emphasize that the RGD derived peptide-Th-1, is capable of inducing in addition to inhibition of micro-vessel sprout formation, cellular signaling of programmed cell death, indicating a possible explanation for the mechanism by which angiogenesis is prevented by Th-1.

As one can see in FIG. 12, apoptosis in the rat-aorta ring was obtained in a dose dependent manner of Th-1 peptide addition. Nuclei staining was performed using a TUNEL procedure. While the control non-treated rat-aorta did not show any staining of the nuclei (FIG. 12(*a*), increased nuclei staining was observed with maximal induction obtained at 250 μg/ml of Th-1 added (FIG. 12(*f*). Total apoptosis was obtained following DNase 1 (1 μg/ml) treatment.

What is claimed is:

1. A method for determining the ability of tumor cells to adhere to extracellular matrix, comprising:
   (a) incubating cells of the tumor, under conditions allowing cell adherence with a compound selected from the group consisting of:
      (i) a fragment of the thrombin B-chain that is active in inhibiting tumor cell adhesion to extracellular matrix comprising the sequence Arg-Gly-Asp in an exposed orientation; and
      (ii) a thrombin that was modified so that residues 187–189 (Arg-Gly-Asp) are in an exposed orientation and that is active in inhibiting tumor cell adhesion to extracellular matrix; and
   (b) determining the level of adherence of the cells to said compound, wherein if said cells adhere to said compound, it indicates the ability of the tumor cells to adhere to extracellular matrix.

2. The method according to claim 1, wherein the fragment of the thrombin B-chain is selected from the group consisting of SEQ ID NO: 1 and SEQ ID NO:2.

3. The method according to claim 1, wherein the tumor is melanoma.

* * * * *